United States Patent [19]

Makela

[11] Patent Number: 5,185,264
[45] Date of Patent: Feb. 9, 1993

[54] DILUENT BUFFER AND METHOD FOR DILUTING AN ASSAY COMPONENT

[75] Inventor: Randal M. Makela, Barrington, Ill.

[73] Assignee: Abbott Laboratories, Abbott Park, Ill.

[21] Appl. No.: 611,222

[22] Filed: Nov. 9, 1990

[51] Int. Cl.$^5$ .............................................. G01N 31/00
[52] U.S. Cl. ..................................... 436/18; 252/308; 252/351; 422/61
[58] Field of Search ............................... 436/18, 8–17; 252/380, 308, 351; 422/61

[56] References Cited

U.S. PATENT DOCUMENTS

| | | | |
|---|---|---|---|
| 3,887,697 | 6/1975 | Vyas et al. | 436/520 |
| 3,914,400 | 10/1975 | Shulman et al. | 436/521 |
| 4,022,667 | 5/1977 | Myrick et al. | 435/19 |
| 4,753,888 | 6/1988 | Chiang | 436/18 |
| 4,760,017 | 7/1988 | McCormick | 435/6 |
| 4,787,963 | 11/1988 | MacConnell | 435/6 |
| 4,822,731 | 4/1989 | Watson et al. | 436/501 |
| 4,849,337 | 7/1989 | Calenoff et al. | 436/513 |
| 4,886,741 | 12/1989 | Schwartz | 436/501 |
| 5,011,770 | 4/1991 | Kung et al. | 435/7.92 |

OTHER PUBLICATIONS

Merck Index, Merck & Co, Inc., Rahway, N.J., 1983, p. 7581.

*Primary Examiner*—James C. Housel
*Assistant Examiner*—Nina Bhat
*Attorney, Agent, or Firm*—Priscilla E. Porembski; Frank S. Ungemach

[57] ABSTRACT

A buffer composition which can be used to dilute assay components and which also can be used when performing immunohematological procedures. The buffer composition includes effective concentrations of phosphate buffer, polyvinylpyrrolidone, cholic acid, bovine serum albumin, a biological detergent and sodium hydroxide, at a pH of from about 5.6 to 7.2. The method of using the buffer composition and a kit containing the buffer composition also is provided.

49 Claims, No Drawings

DILUENT BUFFER AND METHOD FOR DILUTING AN ASSAY COMPONENT

BACKGROUND OF THE INVENTION

This invention relates generally to solutions useful as diluents in the biological sciences which are commonly known as "buffers". Such solutions are capable of neutralizing both acids and bases and thereby maintain the original acidity or basicity of the solution. More particularly, the invention relates to an improved buffer useful for the dilution of immunohematological, immunological and immunochemical assay components, such as antibodies and antigens.

Immunohematological analysis of the blood is performed routinely on the red blood cells of donors and recipients in order to determine whether the red blood cells of a possible blood donor is compatible with with red blood cells an intended recipient. The standard analysis performed in these laboratories is an ABO-Rh blood typing, with the determination of other blood groups, such as Kell and Duffy, sometimes required in order to complete the analysis or so-called "match" of the red blood cells. The ABO blood group is comprised of antigens A and B, with the determination of the blood groups A, B, AB and O based on an agglutination reaction of the test sample with the anti-A, anti-B and anti-A,B antisera. The Rh, or Rhesus blood group comprises several antigens, including the antigens C, D, E, c, and e. Test samples which do not react with anti-D (anti-$Rh_o$) are preliminarily classified as "Rh negative". These presumptive Rh negative test samples are retested with a manual antiglobulin test in which elevated incubation temperature, washing, and the use of a secondary antibody is required to confirm the "negative" result.

No direct agglutination technique, manual or automated, has demonstrated equivalent or greater sensitivity than the manual antiglobulin test with respect to detection of the D antigen. Several attempts have been made to improve the sensitivity of the anti-D reagent in order to eliminate the necessity for performing confirmatory testing. Blood grouping reagent manufacturers have added various components to their reagents to enhance the quality of the agglutination of tests performed in tubes. Thus, for example, a monoclonal IgM anti-D antibody has been included to supplement the human plasma IgG source, with the aim being to provide improved sensitivity for the determination of agglutination of the test sample with anti-D antisera. See, for example, Product insert, Ortho Diagnostics Systems, Blood Grouping Serum Anti-D (Anti-$Rh_o$) (polyclonal and monoclonal blend). However, even the use of this reagent to improve agglutination does not eliminate the need for the use of the confirmatory testing techniques required for anti-D antisera negative determinations, or to dilute the antibody used in the determinations.

Traditional methods for immunohematological analysis which utilize microtiter methods, both manual and automated, require the use of undiluted or low dilutions of the antibody components in order to perform the immunohematological blood group analysis with specificity and sensitivity. No diluent buffer is known to be available commercially for blood grouping reagents. Products are available to add directly to the microplate to increase sensitivity, but these products only are added in conjunction with washing steps and a secondary antibody. See, for example, Product Insert, Gamma Biologicals, Micro-U Enhancement Reagent (Low Ionic) for Antibody Detection tests in Microplates, February (1986). Thus, these methods typically do not offer much of a cost savings to the user, since the user is not able to dilute the reagents required to perform the test.

Other blood group reagent manufacturers have incorporated high molecular weight additives, high protein and surfactants into their reagents to enhance agglutination reactions. Applying these reagents to microplate methodologies, however, also requires no or a very low dilution of antibody reagent in isotonic NaCl or Bovine Serum Albumin (BSA). See, for example, Product Insert, Ortho Diagnostics Systems, Blood Grouping Reagent Anti-D for Slide and Modified Tube Tests, and F. K. Widman, *American Association of Blood Bank Techniques*, "Serologic Techniques and Alloantibodies," pages 435-451 at 440 (1985). Further, pretreatment of the microplate, such as treatment with an anti-static gun or prewetting, previously has been required with some systems. F. K. Widman, *American Association of Blood Bank Techniques*, "Serologic Techniques and Alloantibodies," pages 435-451 at 439 (1985).

SUMMARY OF THE INVENTION

The present invention overcomes the above-identified problems of the prior art by providing an improved buffer useful as a diluent which eliminates the need to perform required confirmatory anti-D testing procedures in cases of a negative or non-reactive result when using a commercially available anti-D antisera or human source antibody. It also provides such a buffer useful for diluting assay components such as antibodies, without sacrificing the sensitivity or specificity of the assay. The buffer of the invention also can be used to dilute out other assay components such as a test sample or an antigen preparation for use in an assay. The buffer provided allows the user the ability to dilute the antibody, for example, to a level not achievable in previous microtiter methods. This dilution of antibody results in both a cost savings to the user, and also serves to preserve the human source antibody which must be used in the majority of blood group antigen testing, where monoclonal antisera are not available. Also, the buffer may be used without pretreatment f the microtiter plate. Thus, treatment with an anti-static gun or prewetting is not required when using the buffer of the present invention.

The present invention accordingly provides an improved buffer solution, comprising a conventional, biological buffer such as a phosphate buffer, a high molecular weight polymer such as polyvinylpyrrolidone (PVP), a biological detergent such as Triton X-100®, bovine serum albumin and sodium chloride all at effective concentrations, and wherein the buffer has a pH in the range of from about pH 5 to about pH 9. Cholic acid is also present in the solution at an effective concentration for visual readout up to four hours after completion of the assay. The buffer also can include sodium azide as a preservative at an effective concentration. The preferred phosphate buffer which is used can comprise sodium phosphate, monobasic and further comprise sodium phosphate, dibasic.

The pH of the buffer of the present invention can range from a pH of about 5.0 to a pH of about 9.0, preferably from about 5.6 to about about 7.2, more preferably the pH is in the range of from about pH 6.0 to about pH 6.8, and most desirably the pH of the buffer is about pH 6.4.

A method of using the buffer provided by the invention comprises diluting the selected assay component(s) in the buffer. A kit containing the buffer as a constituent also is provided.

DETAILED DESCRIPTION OF THE INVENTION

As previously stated, this invention provides an improved buffer which is useful for diluting assay components without sacrificing either the sensitivity or specificity of the assay. The buffer is provided in two compositions. One composition of the buffer is preferred when visual readout up to four hours after completion of the assay is desired. The second composition of the buffer can be used and is preferred when automated assays are to be performed and visual readout is not desired, or when visual readout will be immediate. The latter buffer composition comprises a biological buffer, a high molecular weight polymer, a biological detergent, and bovine serum albumin, all provided at effective concentrations. If visual readout at up to four hours after assay completion is desired, an anionic surfactant is added to the aforedescribed buffer composition in an effective amount. A buffer composition according to the invention has a pH in the range of from about 5 to about 9. Sodium azide may be added to either of the foregoing preferred compositions at an effective concentration to be used as a preservative. If necessary, the overall pH of the buffer of the invention can be adjusted with the addition of an alkaline buffer, such as one containing sodium hydroxide.

The improved biological buffer composition of the invention can include a conventional buffer such as a phosphate buffer, MES (morpholino-ethanesulfonic acid) buffers, BIS-TRIS buffers, citrate buffers, TRIS-HCl buffers and borate buffers, at an effective concentration which can range from about 10 to 100 mM, preferably in the range of from about 10 to 30 mM, and most preferably about 20 mM. The preferred buffer is a phosphate buffer, preferably comprising sodium phosphate, monobasic and sodium phosphate, dibasic, at concentrations such that the effective concentration of buffer is achieved.

Effective concentrations of PVP in the buffer of the invention range from about 0.05 to about 0.25%, (w/v) preferably range from about 0.05 to about 0.15%, and most preferably the concentration is about 0.085%. Effective concentrations of the biological detergent range from about 0.005 to about 0.06%, (w/v) preferably range from about 0.01 to about 0.025%, and most preferably the concentration is about 0.017%. The preferred detergent is Triton X-100 ®. Effective concentrations of cholic acid range from about 0.01 to about 0.3%, (w/v) preferably range from about 0.13 to about 0.2%, and most preferably the concentration of cholic acid is about 0.15%. Bovine Serum Albumin is provided in effective concentrations which range from about 1.5 to about 3.5%, (w/v) preferably in the range of about 1.75 to about 2.75%, and most preferably the concentration of BSA is about 2.25%. Effective concentrations of sodium chloride range from about 0 to about 300 mM, preferably range from about 100 to about 200 mM, and most preferably the concentration of sodium chloride is about 154 mM.

The high molecular weight polymer selected for use in the invention can include polyvinylpyrrolidone (PVP) having molecular weights of from about 10 kd to about 1500 kd, dextrans with molecular weights ranging from about 10 kd to about 2000 kd, polyethylene glycols (PEG) having molecular weights in the range of from about 200 d to about 10,000 d, polyvinyl alcohol having a molecular weight of about 10,000 d to about 100,000 d, polybrene (hexadimethrine bromide), methylcellulose, gum acacia, protamine sulfate, merquat, celquat and magnafloc, provided at an effective concentration. The preferred high molecular weight polymer is polyvinylpyrrolidone (PVP); most preferably, PVP-360 is provided at an effective concentration. The high molecular weight polymers serve as agglutination "enhancers"; the majority of these high molecular weight polymers which can be utilized in the invention have a positive charge, although a positive charge is not necessarily required.

The biological detergents (surfactants) used in the present invention can include non-ionic surfactants, anionic surfactants, zwitterionic surfactants and cationic surfactants. Non-ionic detergents useful in the invention include polyoxyethylene sorbitan monolaurate (Tween ® 20), polyoxyethylene sorbitan monooleate (Tween ® 80), polyoxyethylene ethers(Triton ®, Brij ®)and octylphenel ethylene oxide (Nonidet ®). Anionic surfactants include caprylic acid, cholic acid, dexocholic acid, glycocholic acid and sodium dodecyl sulfate. Zwitterionic surfactants include CHAPS ® (3-[3-Cholamidopropyl)-dimethyl;ammonio]-1-propanesulfonate). Useful cationic detergents include cetylpyridinium chloride. Preferably, non-ionic detergents are used. The most preferred non-ionic detergent is Triton ®X-100. When visual readout is desired for either manual or automatic procedures, the addition of an anionic surfactant to the composition of the buffer is preferred. The most preferred anionic surfactant is cholic acid.

The buffer of the invention is particularly useful as a diluent of assay components. The term "assay components", as used herein, means whole blood or whole blood components including serum, plasma, red blood cells, white blood cells, and platelets. Thus, human and animal test samples or commercial preparations of these components may be diluted with the present buffer. In addition, assay components include commercial assay reagents such as polyclonal and/or monoclonal antibodies, particularly of IgG or IgM class, and fragments thereof; antigens and fragments thereof; antigenic lysates, recombinant proteins, synthetic peptides, and the like. It also is contemplated that inert assay materials, such as latex particles, magnetic beads, microparticle and the like, if provided in a suspension, may be suspended in the buffer of the invention, or if dilution of these materials in a suspension is desired, the dilution may be performed with the buffer of the invention. The buffer also can be used as a substitute for BSA or isotonic NaCl for use in "U"-, "V"-, or flat-bottom microplate systems, whenever the assay procedure calls for dilution of an assay component with these constituents.

The assay component, especially a cell, may be treated prior to dilution with the buffer of the invention with an enzyme such as bromelin, papain, trypsin, chymotrypsin, ficin, neuraminidase, urokinase and the like, or, the assay component may be treated (without enzyme treatment). Preferably, the assay component is treated with an enzyme in order to optimally use the buffer of the invention to its maximum capability, especially when performing agglutination assays. Preferably, the enzyme used is bromelin.

The buffer provided by the invention may be used to dilute assay components prior to performing the assay itself, or, it can be used to dilute assay components when performing the assay, such as when serial dilutions of test sample or other assay components are performed according to a particular assay method. The buffer provided is especially useful for diluting antibodies which are used in determining the presence or absence of specific antigens on red blood cells (erythrocytes). When antibody is diluted with the buffer of the invention, it allows the red blood cells possessing the specific antigen and present in the test sample to agglutinate with the antibody. The agglutination (clumping) of the red blood cells indicates a positive reaction, while no agglutination, indicated by a uniform cell suspension, indicates a negative reaction. Non-specific reactivity has not been found while employing the buffer as a diluent. In the past, antibody testing such as described above, and performed against human source polyclonal plasma, has required that an additional control test be performed in which the test sample is tested against the supplementary components present in commercial antibody reagents in order to determine whether the test sample reacts with the commercial antibody component itself or with the supplementary components. Preliminary test results obtained with two rare known samples which react with supplementary components indicate, however, that when the present buffer is used, this additional testing need not be performed, since the test samples diluted with the buffer of the invention do not react with the supplementary components.

Other advantages of the buffer provided by the present invention have been disclosed. For Example, the present buffer can be used when testing for the presence of the D antigen on red blood cells. It has been determined that the sensitivity of the results is increased such that no additional testing is required to confirm the result, thus eliminating the standard procedure of confirmatory testing which is the conventional procedure used when employing microplate testing methodologies. The buffer also can be used in other antigen-antibody interactions to enhance the reactions, such as for Hepatitis Surface Antigen and Syphillis testing.

It has been found that the reagents comprising the buffer of the invention can vary significantly in concentration without detracting from the performance of the buffer in assays. Table 1 lists the reagent components of the buffer and their range of effective concentrations.

These concentrations are based on a 60 $\mu l$ diluted antibody per test, and 30 $\mu l$ red cell suspension (3 to 5%). It is understood that the component cholic acid is not required for performance of the buffer as a diluent when visual readout for up to four hours is not desired. Thus, cholic acid may be removed from the buffer composition in this situation. Sodium chloride may be used to adjust the pH. Therefore, sodium chloride may be provided as follows:

| Component | Concentration Range (from about ... to about) | Preferred Concentration Range (from about ... to about) |
| --- | --- | --- |
| NaCl | 0 to 300 mM | 100 to 200 mM Most Preferred Conc: 154 mM |

In its most preferred composition for visual readout, the buffer is provided at the following concentration.

| Formulation of the Buffer for Visual Readout: | |
| --- | --- |
| Materials: | Diluent Buffer, 10 liter (L) preparation size: |
| Sodium Phosphate, Monobasic | 22.1 grams (0.221% w/v) |
| Sodium Phosphate, Dibasic | 5.62 grams (0.056% w/v) |
| Sodium Chloride | 90.0 grams (0.9% w/v) |
| PVP-360 | 8.5 grams (0.085% w/v) |
| Cholic Acid | 15.0 grams (0.15% w/v) |
| Bovine Serum Albumin (BSA) | 225.0 grams (2.25% w/v) |
| Triton X-100 ® (10%) | 17.0 milliliters (ml) (0.17% w/v) |

Procedure

To approximately 8 liters of Di water, add the Sodium Phosphate, Monobasic and the Sodium Phosphate, Dibasic, and mix until dissolved. Then add the Sodium Chloride to the mixture and mix again until dissolved. Add the PVP-360 next and vigorously mix. Following that addition, add the Cholic Acid and mix unit it is dissolved. Then, add the BSA and mix until it is dissolved. Finally, add the Triton-X100 ® and mix until it is dissolved, which mixing is accomplished in approximately 15 minutes. Adjust the mixture to pH 6.4 with Sodium Hydroxide. Q.S. to 10 L. If visual readout is not required, the cholic acid may be deleted from the formula, and the concentration of Triton may be increased within the range provided herein. If the presence of sodium azide is desired, then 10.0 grams (0.1% w/v) of sodium azide is added to the buffer when add-

TABLE 1

| Component | Concentration Range (from about ... to about) | Preferred Concentration Range (from about ... to about) |
| --- | --- | --- |
| Polyvinylpyrrolidone | 0.005 to 0.25% (w/v) | 0.05 to 0.15%K Value 90, MW 100–1500K, Most Preferred Conc.: 0.085% |
| Triton X-100 ® | 0.005 to 0.06% (w/v) | 0.01 to 0.025% Most Preferred Conc: 0.017% |
| Cholic Acid | 0.01 to 0.3% (w/v) | 0.13 to 0.2% Most Preferred Conc.: 0.15% |
| BSA | 1.5 to 3.5% (w/v) | 1.75 to 2.75% Most Preferred Conc.: 2.25% |
| Phosphate Buffer (Sodium Phosphate, Monobasic and Sodium Phosphate, Dibasic) | 10 to 100 mM | 10 to 30 mM Most Preferred Conc.: 20 mM |
| pH | 5.0 to 9.0 | 5.6 to 7.2; 6.0 to 6.8; Most Preferred pH: 6.4 | ing sodium chloride. The pH of the buffer may be adjusted with sodium hydroxide.

It has been found, for example, that the effective antibody dilution range varies from 1:2 to about 1:100,000. The effective dilution range will vary depending upon the assay component being diluted; it is contemplated, however, that dilutions greater than 1:100,000, and up to approximately 1:500,000, will be able to be achieved with the present buffer using different assay components. This dilution may be performed prior to performing the assay itself. It also is contemplated that the buffer can be used to dilute components such as antibodies, test samples, or antigens, when performing the assay itself, such as when serial dilutions of test sample or other possible assay components are performed according to assay method.

The present invention now will be described by way of examples, which are meant to illustrate preferred embodiments of the invention, but not to limit the spirit and scope thereof.

EXAMPLES

Example 1

Sensitivity of buffer with commercial antisera: automated assay

An evaluation of commercially available antisera diluted in the buffer of the invention (provided in the preferred format, with cholic acid and sodium azide) was performed using a prototype automated blood bank analyzer (prototype of Abbott Laboratories, Abbott Park. Ill. 60064). Five commercially available antisera (anti-D, anti-C, anti-E, anti-c and anti-e), were serially diluted. Each dilution was tested against four homozygous, 4 heterozygous and one antigen negative donor samples. The materials used in the experiment were as follows: The buffer of the invention, provided as described herein; anti-D (Ortho Diagnostics Bioclone$\phi$, Lot No. DB113A), anti-C (Ortho Diagnostics, Lot. No. CS163B), anti-E (Ortho Diagnostics, Lot No. ES124B), anti-c (Ortho Diagnostics, Lot No. SC826A), anti-e (Ortho Diagnostics, Lot No. SE133A). The assays sere performed in microtiter trays. The phenotypes of the test cells were unknown at the time of performing the experiment. The test cells provided were analyzed at the Blood Center of Southeaster Wisconsin (Milwaukee, Wis.) for complete Rh-hr phenotype prior to testing at Abbott Laboratories; however, the test cells were coded prior to testing at Abbott Laboratories in order to avoid any subjectivity when determining titers. Each diluted antisera was tested against the following coded test cells using the instruction sheet send from the Blood Center.
Anti-D Plate: Cells labelled as A, B, D, E, F, H, I, J, M
Anti-C Plate: Cells labelled as A, C, D, E, H, I, J, L, O
Anti-E Plate: Cells labelled as C, D, F, J, M, N, O, Q, R
Anti-c Plate: Cells labelled as A, B, D, E, G, I, K, O, P
Anti-E Plate: Cells labelled as C, D, F, H, I, M, N, O, P The test cell diluent comprised the following:
b 7.5 mls of 2% Bromelin (obtained from Sigma Chemical Co., St. Louis, Mo., lot No. 37033-15),
1.0 mls of 1% Tween® 20 (obtained from Sigma Chemical Co., St. Louis, Mo., lot No. 21197-12), and
91.5 mls of 0.9% NaCl, 0.1% Sodium Azide Serial two-fold dilutions were prepared individually using each of the antisera described herein and following the procedure outlined in the AABB Technical Manual, 9th Edition, page 239. The dilutions prepared ranged from 1:2 to 1:131072. The dilutions were utilized in performing red cell phenotyping with a prototype automated blood bank analyzer (prototype of Abbott Laboratories, Abbott Park, Ill. 60064).

The automated blood bank analyzer format comprised a track which functioned as a "conveyor-type" mechanism, in which microtiter trays were placed on a track and advanced from station to station at 4.8 minute intervals.

Station 1 was a reagent station. 60 $\mu$l of antisera reagent was dispensed, in its diluted form, to the designated locations on the microtiter tray. In addition, 230 $\mu$l bromelin reagent was dispensed to three cell dilution wells. One well was designated as a primary dilution well wherein packed red cells from a "pilot" tube that contained whole blood which had been centrifuged to pellet the red cells were placed.

Station 2 was the sample handling station. 70 $\mu$l of packed red cells were pipetted from the pilot tube to the primary cell dilution well which contained 230 $\mu$l of bromelin solution. The cell suspension was mixed by aspirating and dispensing within the pipet itself.

Station 3 was the cell diluter/distributor. 70 $\mu$l of the primary cell dilution (approximately a 15.4% cell concentration) was transferred to the two secondary dilution wells for each test sample. The secondary dilution wells were mixed, and 30 $\mu$l of these suspensions (approximately 4–5% cell concentration) were distributed to the designated test wells.

The tray was then transported along the following track:
Station 4—Horizontal
Station 5—50° tilt in direction A
Station 6—50° tilt in direction B
Station 7—65° tilt in direction A
Station 8—Horizontal
Station 9—65° tilt in direction B
Station 10—Horizontal
Station 11—50° tilt in direction A
Station 12—Horizontal
Station 13—The tray was read for the presence or absence of cells in the light path.

A positive result was determined to be high light counts, in which crescent-shaped agglutinates formed, and a negative result was determined to be low light counts, in which uniform cell suspension was present.

Eight cells were tested per tray. Two separate trays were required for the number of antisera dilutions tested. Tray #1 contained dilutions 1:2 through 1:4096. Tray #2 contained dilutions 1:8192 through 1:131,072.

Tables 2-6 show data which demonstrate that the commercially available antisera can be diluted to a great extent when utilizing the buffer of the invention.

TABLE 2

| Coded Sample | Anti-D Diluent | Expected Result |
| --- | --- | --- |
| A | 16,394 | + |
| B | 0 | 0 |
| D | 32,768 | + |
| E | 32,768 | + |
| F | 32,768 | + |
| H | 32,768 | + |
| I | 16,384 | + |
| J | 16,384 | + |

TABLE 2-continued

| Coded Sample | Anti-D Diluent | Expected Result |
|---|---|---|
| M | 32,768 | + |

TABLE 3

| Coded Sample | Anti-C Diluent | Expected Result |
|---|---|---|
| A | 2,048 | + |
| C | 2,048 | + |
| D | 2,048 | + |
| E | 2,048 | + |
| H | 2,048 | + |
| I | 2,048 | + |
| J | 0 | 0 |
| L | 4,096 | + |
| O | 4,096 | + |

TABLE 4

| Coded Sample | Anit-E Diluent | Expected Result |
|---|---|---|
| C | 0 | 0 |
| D | 512 | + |
| F | 512 | + |
| J | 512 | + |
| M | 512 | + |
| N | 1,024 | + |
| O | 1,024 | + |
| Q | 512 | + |
| R | 512 | + |

TABLE 5

| Coded Sample | Anti-c Diluent | Expected Result |
|---|---|---|
| A | 4,096 | + |
| B | 8,192 | + |
| D | 8,192 | + |
| E | 0 | 0 |
| G | 8,192 | + |
| I | 8,192 | + |
| K | 8,192 | + |
| O | 8,192 | + |
| P | 16,394 | + |

TABLE 6

| Coded Sample | Anit-e Diluent | Expected Result |
|---|---|---|
| C | 1,024 | + |
| D | 1,024 | + |
| F | 512 | + |
| H | 512 | + |
| I | 512 | + |
| M | 128 | + |
| N | 0 | 0 |
| O | 512 | + |
| P | 1,024 | + |

Example 2
Sensitivity of buffer with donor antisera: manual methods

Assays were manually performed at the Southeastern Blood Center of Wisconsin following the procedures detailed in the AABB Technical Manual, 9th Edition, page 239. The test cells were treated with Ficin at 0.5% prior to assay. The assays were performed in U-bottom microtiter plates on donor plasma. Visual interpretation of results was performed. The antibodies tested were the same as described in Example 1. Each diluted antisera was tested against the same panel as that described in Example 1. In addition to testing with the buffer of the invention, a 3% BSA buffer also was tested. The results are detailed below in Tables 7–11.

TABLE 7

| Coded Sample | Anti-D Testing (Endpoint Dilution Results) | |
|---|---|---|
| | 3% BSA | Buffer |
| A | 2,048 | 16,394 |
| B | 0 | 0 |
| D | 4,096 | 16,394 |
| E | 4,096 | 16,394 |
| F | 4,096 | 16,394 |
| H | 2,048 | 16,394 |
| I | 2,048 | 16,394 |
| J | 4,096 | 8,192 |
| M | 1,024 | 8,192 |

TABLE 8

| Coded Sample | Anti-C Testing (Endpoint Dilution Results) | |
|---|---|---|
| | 3% BSA | Buffer |
| A | 2,048 | 4,096 |
| C | 4,096 | 8,192 |
| D | 2,048 | 8,192 |
| E | 4,096 | 8,192 |
| H | 4,096 | 8,192 |
| I | 2,048 | 8,192 |
| J | 0 | 0 |
| L | 4,096 | 16,394 |
| O | 1,024 | 8,192 |

TABLE 9

| Coded Sample | Anti-E Testing (Endpoint Dilution Results) | |
|---|---|---|
| | 3% BSA | Buffer |
| C | 0 | 0 |
| D | 64 | 128 |
| F | 64 | 128 |
| J | 128 | 256 |
| M | 64 | 128 |
| N | 128 | 256 |
| O | 128 | 256 |
| Q | 128 | 128 |
| R | 128 | 64 |

TABLE 10

| Coded Sample | Anti-c Testing (Endpoint Dilution Results) | |
|---|---|---|
| | 3% BSA | Buffer |
| A | 512 | 2,048 |
| B | 512 | 8,192 |
| D | 512 | 8,192 |
| E | 0 | 0 |
| G | 512 | 16,394 |
| I | 512 | 4,096 |
| K | 1,024 | 8,192 |
| O | 512 | 8,192 |
| P | 1,024 | 8,192 |

TABLE 11

| Coded Sample | Anti-e Testing (Endpoint Dilution Results) | |
|---|---|---|
| | 3% BSA | Buffer |
| C | 1,024 | 2,048 |
| D | 1,024 | 4,096 |
| F | 1,024 | 4,096 |
| H | 2,048 | 8,192 |
| I | 2,048 | 8,192 |
| M | 1,024 | 4,096 |
| N | 0 | 0 |
| O | 1,024 | 8,192 |
| P | 1,024 | 8,192 |

Example 3

Du phenotyping in an automated system sensitivity of buffer compared to BSA

This experiment was performed to compare and contrast the performance of 3% BSA and the buffer diluent when utilized in Du phenotyping on an automated bidirectional tilt system as described in Example 1. The more sensitive buffer, in this context, was defined as the buffer which allowed the utilization of the lower amount of antibody to detect the presence of the Du phenotype by agglutination technology. To those skilled in the art, Du is classified as a red blood cell possessing the D antigen in which the presence of the D antigen cannot be demonstrated by using initial testing methods and, therefore, it requires more detailed testing to demonstrate its presence, such as by Indirect Antiglobulin Methodology. This definition of Du can depend both on the methodology used, (manual or automated), and also on the antisera source used. Du is defined in this experiment as red cell samples initially screened D negative on Dynatech Microbank Systems (Badger Region Red Cross, Madision, Wis.), and retested to be D positive by Indirect Antiglobulin Test.

The experiment followed the procedure of Example 1 with the following changes. Only a single antisera was tested, Ortho Diagnostics' Slide Anti-D, lot no. D5670D. The method of preparing a two-fold serial dilution was performed as in Example 1, with the exception that the initial dilution was 1:6.25. This dilution method is described in the AABB Technical Manual, 9th Edition, p. 239. (Technique for Master Dilution [1985]).

In the past, there have been inherent problems with utilizing commercially available antisera in microplate methodology, manual or automated. The antisera has needed to be diluted such that the additives which are incorporated into the antisera reagent are diluted out to a satisfactory level to eliminate false positive reactions (agglutination in the absence of specific antibody). Thus, controls were necessary to prove that, at low dilutions, there was specific agglutination occurring. As the additives were diluted out further, and the amount of diluent present overcame those additives, no non-specific agglutination occurred at higher dilutions. The level of non-specific agglutination which would occur with both the diluent buffer and 3% BSA when the commercial antisera were diluted in them was initially determined. The levels of dilution at which non-specific agglutination occurred were 1:12.5 with 3% BSA and 1:25 with the diluent buffer. All positive reactions above these dilutions were considered true positive results, and all reactions at or below are to be considered false positive results.

The results of the comparison are shown in Table 12.

TABLE 12

Du Testing With Diluent vs. 3% BSA Anti-D dilution

| Specimen # | 3% BSA | Diluent |
|---|---|---|
| 1 | 50 | 1,600 |
| 2 | 400 | 3,200 |
| 3 | 50 | 800 |
| 4 | 100 | 1,600 |
| 5 | 50 | 800 |
| 6 | 100 | 1,600 |
| 7 | 400 | 3,200 |
| 8 | 1,600 | 12,800 |

TABLE 12-continued

Du Testing With Diluent vs. 3% BSA Anti-D dilution

| Specimen # | 3% BSA | Diluent |
|---|---|---|
| 9 | 50 | 800 |
| 10 | 100 | 1,600 |
| 11 | 200 | 1,600 |
| 12 | 50 | 800 |
| 13 | 100 | 400 |
| 14 | 400 | 3,200 |
| 15 | 100 | 1,600 |
| 16 | 100 | 1,600 |
| 17 | 25 | 800 |
| 18 | 25 | 200 |
| 19 | 100 | 800 |
| 20 | not detected | 200 |
| 21 | 200 | 3,200 |
| 22 | 400 | 3,200 |
| 23 | 400 | 6,400 |
| 24 | 50 | 800 |
| 25 | 25 | 800 |
| 26 | 50 | 800 |
| 27 | 100 | 800 |
| 28 | 50 | 800 |
| 29 | 800 | 3,200 |
| 30 | 25 | 400 |
| 31 | 50 | 800 |
| 32 | 100 | 800 |
| 33 | not detected | 400 |
| 34 | 100 | 800 |
| 35 | 100 | 800 |
| 36 | 100 | 800 |
| 37 | 25 | 400 |
| 38 | 50 | 800 |
| 39 | 400 | 1,600 |
| 40 | not detected | 800 |
| 41 | 25 | 400 |
| 42 | 100 | 800 |
| 43 | 25 | 400 |
| 44 | not detected | 200 |
| 45 | 25 | 400 |
| 46 | 50 | 800 |
| 47 | 50 | 800 |
| 48 | not detected | 800 |
| 49 | 25 | 1,600 |
| 50 | 100 | 1,600 |
| 51 | 200 | 1,600 |
| 52 | 400 | 1,600 |
| 53 | 25 | 400 |
| 54 | 25 | 400 |
| 55 | 200 | 800 |
| 56 | not detected | 400 |
| 57 | 1,600 | 12,800 |
| 58 | 100 | 1,600 |
| 59 | 100 | 800 |
| 60 | 200 | 1,600 |
| 61 | 200 | 1,600 |
| 62 | 50 | 800 |
| 63 | 800 | 3,200 |
| 64 | 100 | 800 |
| 65 | 200 | 1,600 |
| 66 | 50 | 800 |
| 67 | 50 | 400 |
| 68 | 25 | 400 |
| 69 | 25 | 400 |
| 70 | 50 | 400 |
| 71 | 100 | 400 |

It will be apparent to one of ordinary skill in the art to which this invention pertains that various changes and modifications can be made in the specifically-described embodiments of the invention disclosed herein, without departing from the spirit and scope of the invention, which is defined solely by the following claims:

What is claimed is:

1. A buffer composition comprising:
   a phosphate buffer at an effective concentration;

a high molecular weight polymer, selected from the group consisting of polyvinylpyrrolidone, dextrans, polyethylene glycols, polyvinyl alcohol, polybrene (hexadimethrine bromide), methylcelluloses, gum acacia, protamine sulfate, merquat, celquat, and magna floc at an effective concentration;

a non-ionic selected from the group consisting of polyoxyethylene sorbitan monolaurate (Tween ® 20), polyoxyethylene sorbitan monooleate (Tween ® 80), polyoxyethylene ethers (Triton ®, Brij ®) and octylphenol ethylene oxide surfactant at an effect concentration;

an anionic surfactant caprylic acid, cholic acid, dexocholic acid, glycocholic acid and sodium dodecyl sulfate at an effective concentration;

bovine serum albumin at an effective concentration; and sodium chloride at an effective concentration; such that the pH of the buffer composition is in the range of from about pH 5 to about pH 9.

2. The buffer composition of claim 1 wherein the effective concentration of phosphate buffer is in the range of from about 10 to about 100 mM.

3. The buffer composition of claim 2 wherein the effective concentration of phosphate buffer is in the range of from about 10 to about 30 mM.

4. The buffer composition of claim 1 wherein the phosphate buffer comprises sodium phosphate monobasic and sodium dibasic at an effective concentration.

5. The buffer composition of claim 1 wherein the high molecular weight polymer is polyvinylpyrrolidone at a concentration in the range of from about 0.005 to about 0.25% (w/v).

6. The buffer composition of claim 5 wherein the polyvinylpyrrolidone is at a concentration in the range of from about 0.05 to about 0.15% (w/v).

7. The buffer composition of claim 1 wherein the non-ionic surfactant is at a concentration in the range of from about 0.005 to about 0.03% (w/v).

8. The buffer composition of claim 7 wherein the non-ionic surfactant is Triton X-100 at a concentration in the range of from about 0.01 to about 0.025% (w/v).

9. The buffer composition of claim 1 wherein said anionic surfactant is cholic acid at a concentration in the range of from about 0.01 to about 0.3% (w/v).

10. The buffer composition of claim 9 wherein the cholic acid is at a concentration in the range of from about 0.13 to about 0.2% (w/v).

11. The buffer composition of claim 1 wherein the bovine serum albumin is at a concentration in the range of from about 1.5 to about 3.5% (w/v).

12. The buffer composition of claim 11 wherein the bovine serum albumin is at a concentration in the range of from about 1.75 to about 2.75% (w/v).

13. The buffer composition of claim 1 wherein the pH of the buffer is in the range of from about pH 5.6 to pH 7.2.

14. The buffer composition of claim 13 wherein the pH of the buffer is about 6.4

15. The buffer composition of claim 1 wherein said sodium chloride is at a concentration in the range of from about 0 to about 300 mM.

16. The buffer composition of claim 15 wherein the concentration of said sodium chloride is in the range of from about 100 to about 300 mM.

17. The buffer composition of claim 1 further comprising sodium azide at an effective concentration.

18. The buffer composition of claim 17 wherein sodium azide is at a concentration of about 0.1% (w/v).

19. A buffer composition comprising:
polyvinylpyrrolidone in an effective concentration in the range of from about 0.05 to about 0.15% (w/v);
polyoxyethylene ether (Triton X-100 ®) in an effective concentration in the range of from about 0.01 to about 0.025% (w/v);
cholic acid in an effective concentration in the range of from about 0.13 to about 0.2% (w/v);
bovine serum albumin in an effective concentration in the range of from about 1.75 to about 2.75% (w/v);
phosphate buffer in an effective concentration in the range of from about 10 to about 30 mM; and
sodium chloride in an effective concentration in the range of from about 100 to about 200 mM; such that the pH of the buffer is in the range of from about 6.0 to about pH 6.8.

20. The buffer composition of claim 19 wherein the phosphate buffer comprises sodium phosphate monobasic and sodium phosphate dibasic.

21. The buffer composition of claim 19 further comprising sodium azide at an effective concentration of about 0.01% (w/v).

22. A buffer composition comprising:
sodium phosphate, monobasic at approximately 0.22% (w/v);
sodium phosphate, dibasic at approximately 0.056% (w/v);
sodium chloride at approximately 0.9% (w/v);
polyvinylpyrrolidone at a concentration of about 0.085% (w/v);
cholic acid at a concentration of about 0.15% (w/v);
bovine serum albumin at a concentration of about 2.25% (w/v); and
polyoxyethylene ether (Triton X-100 ®) at a concentration of about 0.017% (w/v); wherein the pH of the buffer is approximately 6.4.

23. The buffer composition of claim 22 further comprising sodium azide at a concentration of about 0.1% (w/v).

24. A method for diluting an assay component, which method comprises mixing a known amount of an assay component with a known amount of a buffer composition, said buffer composition comprising:
a phosphate buffer at an effective concentration;
a high molecular weight polymer selected from the group consisting of polyvinylpyrrolidone, dextrans, polyethylene glycols, polyvinyl alcohol, polybrene (hexadimethrine bromide), methylcelluloses, gum acacia, protamine sulfate, merquat, celquat, and magna floc at an effective concentration;
a non-ionic surfactant selected from the group consisting of polyoxyethylene sorbitan monolaurate (Tween ® 20), polyoxyethylene sorbitan and monooleate (Tween ® 80), polyoxyethylene ethers (Triton ®, Brij ®) and octylphenol ethylene oxide at an effective concentration;
an anionic surfactant caprylic acid, cholic acid, dexocholic acid, glycocholic acid and sodium dodecyl sulfate at an effective concentration;
Bovine Serum Albumin at an effective concentration;
Sodium Chloride at an effective concentration; such that the pH of the buffer is in the range of from about pH 5.0 to about pH 9.

25. The method of claim 24 wherein the effective combination of said phosphate buffer is in the range of from about 10 to about 100 mM.

26. The method of claim 25 wherein the effective concentration of said phosphate buffer in the range of from about 10 to about 30 mM.

27. The method of claim 24 wherein said phosphate buffer is comprised of sodium phosphate monobasic and sodium phosphate dibasic.

28. The method of claim 24 wherein said high molecular weight polymer is polyvinylpyrrolidone at a concentration in the range of from about 0.05 to about 0.25% (w/v).

29. The method of claim 28 wherein said polyvinylpyrrolidone concentration is in the range of from about 0.05 to about 0.15% (w/v).

30. The method of claim 24 wherein the non-ionic surfactant is polyoxyethylene ether (Triton X-100®) at a concentration in the range of from about 0.005 to about 0.03% (w/v).

31. The method of claim 30 wherein the concentration of said polyoxyethylene ether (Triton X-100®) is in the range of from about 0.01 to about 0.25% (w/v).

32. The method of claim 24 wherein the anionic surfactant is cholic acid at a concentration in the range of from about 0.01 to about 0.3% (w/v).

33. The method of claim 32 wherein the cholic acid is at a concentration in the range of from about 0.13 to about 0.2% (w/v).

34. The method of claim 24 wherein said bovine serum albumin is at a concentration in the range of from about 1.5 to about 3.5% (w/v).

35. The method of claim 34 wherein the bovine serum albumin is at a concentration in the range of from about 1.75 to about 2.75% (w/v).

36. The method of claim 24 wherein the pH of the buffer is in the range of from about pH 6.0 to about pH 6.8.

37. The method of claim 24 wherein said sodium chloride at a concentration in the range of from about 0 to 300 mM.

38. The method of claim 37 wherein the concentration of said sodium chloride is in the range of from about 100 to 300 mM.

39. The method of claim 24 wherein the buffer further comprises sodium azide at an effective concentration.

40. The method of claim 39 wherein said sodium azide is at a concentration of about 0.1% (w/v).

41. The method of claim 25 wherein said assay component is selected from the group consisting of an antibody or fragment thereof, an antigen or fragment thereof, a whole blood component, an antigenic lysate, a recombinant protein and a synthetic peptide.

42. A composition for performing assays, comprising:
a buffer composition comprising:
phosphate buffer at an effective concentration;
a high molecular weight polymer selected from the group consisting of polyvinylpyrrolidone, dextrans, polyethylene glycols, polyvinyl alcohol, polybrene (hexadimethrine bromide), methylcelluloses, gum acacia, protamine sulfate, merquat, celquat, and magna floc at an effective concentration;
a non-ionic selected from the group consisting of polyoxyethylene sorbitan monolaurate (Tween® 20), polyoxyethylene sorbitan and monooleate (Tween® 80), polyoxyethylene ethers (Triton®, Brij®) and octylphenol ethylene oxide surfactant at an effective concentration;
an anionic surfactant caprylic acid, cholic acid, dexocholic acid, glycocholic acid and sodium dodecyl sulfate at an effective concentration;
bovine serum albumin at an effective concentration; and
sodium chloride at an effective concentration; such that the pH of the buffer is in the range of from about pH 5 to about pH 9.

43. The composition of claim 42 further comprising sodium azide at a concentration of about 0.1% (w/v).

44. The composition of claim 43 wherein said phosphate buffer is at a concentration in the range of from about 10 to about 30 mM.

45. The composition of claim 43 wherein said high molecular weight polymer is polyvinylpyrrolidone at a concentration in the range of from about 0.05 to about 0.15% (w/v).

46. The composition of claim 43 wherein said anionic surfactant is cholic acid at a concentration of from about 0.13 to about 0.2% (w/v).

47. The composition of claim 43 wherein said nonionic surfactant is polyoxyethylene ether (Triton X-100®) at a concentration in the range of from about 0.01 to about 0.025%. (w/v).

48. The composition of claim 43 wherein said bovine serum albumin is at a concentration in the range of from about 1.75 to about 2.75% (w/v).

49. The composition of claim 43 wherein said sodium chloride is at a concentration in the range of from about 100 to about 300 mM.

* * * * *

UNITED STATES PATENT AND TRADEMARK OFFICE
CERTIFICATE OF CORRECTION

PATENT NO. : 5,185,264
DATED : February 9, 1993
INVENTOR(S) : Randal M. Makela

It is certified that error appears in the above-indentified patent and that said Letters Patent is hereby corrected as shown below:

Column 2, line 3, change "Detection tests in Microplates" to -- Detection Tests in Microplates--.

Column 4, line 27, change "octylphenel ethylene oxide" to --octylphenol--ethylene oxide --.

Column 7, line 24, change "buffer with commercial antisera:" to -- Buffer with Commercial Antisera: --.

Column 7, line 25, change "automated assay" to -- Automated Assay --.

Column 7, line 37, change "(Ortho Diagnostics Bioclone∅," to -- (Ortho Diagnostics Bioclone® --.

Column 7, line 41, change "The assays sere" to -- The assays were --.

Column 7, line 45, change "Southeaster Wisconsin " to -- Southeastern Wisconsin --.

Column 7, line 57, change "Anti-E Plate:" to -- Anti-e Plate: --.

UNITED STATES PATENT AND TRADEMARK OFFICE
CERTIFICATE OF CORRECTION

PATENT NO. : 5,185,264
DATED : February 9, 1993
INVENTOR(S) : Randal M. Makela

It is certified that error appears in the above-indentified patent and that said Letters Patent is hereby corrected as shown below:

Column 7, line 60, change " b 7.5 mls of 2% Bromelin" to

-- 7.5 mls of 2% Bromelin --.

Column 9, line 60, change "buffer with donor antisera: manual" to

-- Buffer with Donor Antisera: Manual --.

Column 9, line 61, change "methods" to

-- Methods --.

Column 11, line 3, change "automated system sensitivity" to

-- Automated System Sensitivity --.

Column 11, line 4, change "buffer compared to" to

-- Buffer Compared to --.

Signed and Sealed this

Twenty-sixth Day of April, 1994

Attest:

BRUCE LEHMAN

*Attesting Officer*   *Commissioner of Patents and Trademarks*